(12) United States Patent
Ishigaki et al.

(10) Patent No.: US 10,495,438 B2
(45) Date of Patent: Dec. 3, 2019

(54) MEASUREMENT DEVICE

(71) Applicant: CKD CORPORATION, Aichi (JP)

(72) Inventors: Hiroyuki Ishigaki, Aichi (JP);
Takahiro Mamiya, Aichi (JP)

(73) Assignee: CKD CORPORATION, Aichi (JP)

( * ) Notice: Subject to any disclaimer, the term of this patent is extended or adjusted under 35 U.S.C. 154(b) by 0 days.

(21) Appl. No.: 16/279,297

(22) Filed: Feb. 19, 2019

(65) Prior Publication Data
US 2019/0178625 A1  Jun. 13, 2019

Related U.S. Application Data

(63) Continuation of application No. PCT/JP2017/015870, filed on Apr. 20, 2017.

(30) Foreign Application Priority Data

Aug. 24, 2016  (JP) .................... 2016-163220

(51) Int. Cl.
*G01B 9/02* (2006.01)
*G01B 11/02* (2006.01)
(Continued)

(52) U.S. Cl.
CPC .............. *G01B 9/02* (2013.01); *G01B 11/026* (2013.01); *G01B 11/14* (2013.01); *G01B 11/2545* (2013.01); *G06T 1/00* (2013.01)

(58) Field of Classification Search
CPC ............ G01B 9/02041; G01B 9/02083; G01B 9/02084; G01B 9/02085; G01B 9/02087; G01B 2290/70
See application file for complete search history.

(56) References Cited

U.S. PATENT DOCUMENTS 6,002,480 A * 12/1999 Izatt .................... G01J 3/4412
356/479
2010/0166293 A1 * 7/2010 Sugita .................... A61B 3/102
382/154
(Continued)

FOREIGN PATENT DOCUMENTS

JP   H08-219722 A   8/1996
JP   H11-337321 A   12/1999
(Continued)

OTHER PUBLICATIONS

International Preliminary Report on Patentability issued in corresponding International Application No. PCT/JP2017/015870 dated Feb. 26, 2019, with translation (9 pages).
(Continued)

*Primary Examiner* — Jonathan M Hansen
(74) *Attorney, Agent, or Firm* — Osha Liang LLP

(57) ABSTRACT

A measurement device includes: an optical system that splits incident light into two lights to emit one light as measurement light to a measurement object and the other light as reference light to a reference surface, and recombines the two lights to emit combined light; a light emitter that emits light entering the optical system; an imaging system that takes an image of output light emitted from the optical system; and a processor that executes measurement with regard to a predetermined measurement area of the measurement object, based on an interference fringe image taken by the imaging system, wherein the processor: obtains complex amplitude data at a predetermined position in an optical axis direction at predetermined intervals in at least a predetermined range in the optical axis direction, with regard to a specific area set in advance in the measurement area based on the interference fringe image.

15 Claims, 7 Drawing Sheets

(51) Int. Cl.
*G01B 11/14* (2006.01)
*G01B 11/25* (2006.01)
*G06T 1/00* (2006.01)

(56) References Cited

U.S. PATENT DOCUMENTS

2011/0199615 A1* 8/2011 Sugita ............... A61B 3/102
 356/456
2017/0105618 A1* 4/2017 Schmoll ............ A61B 3/1025

FOREIGN PATENT DOCUMENTS

| | | |
|---|---|---|
| JP | 2003-232619 A | 8/2003 |
| JP | 2005-24432 A | 1/2005 |
| JP | 2010-25663 A | 2/2010 |
| JP | 2016-504947 A | 2/2016 |

OTHER PUBLICATIONS

International Search Report for corresponding International Application No. PCT/JP2017/015870, dated Aug. 1, 2017 (3 pages).

* cited by examiner

MEASUREMENT DEVICE

BACKGROUND

Technical Field

The present invention relates to a measurement device configured to measure the shape of a measurement object.

Description of Related Art

A measurement device using an interferometer has been conventionally known as one measurement device configured to measure the shape of a measurement object (as described in, for example, Patent Literature 1). Among them, there is also provided a measurement device configured to perform measurement by the phase shift method, based on a plurality of interference fringe images having different phases (as described in, for example, Patent Literature 2).

A failure in appropriately placing a measurement object in a focusing range of an imaging unit is, however, likely to fail to obtain focused image data of high accuracy and decrease the measurement accuracy.

Conventionally, there is accordingly a need to execute a preliminary process of placing the measurement object in the focusing range with high accuracy, prior to a start of measurement. This is likely to increase the total time period required for measurement. The measurement range for height measurement may be restricted by the focusing range.

A recently proposed interference imaging device has a function of correcting an out-of-focus aberration (as described in, for example, Patent Literature 3). Correcting the out-of-focus aberration converts out-of-focus image data into focused image data by an arithmetic operation and thereby gives image data of high accuracy. As a result, this improves the measurement accuracy.

CITATION LIST

Patent Literatures

PTL 1: JP H08-219722A
PTL 2: JP H11-337321A
PTL 3: JP 2016-504947A

The prior art technique described in Patent Literature 3 is configured to generate aberration-corrected images with regard to a plurality of positions in an optical axis direction (height direction) in a predetermined range in the optical axis direction where a measurement object is allowed to be located and to extract a focused image among the generated aberration-corrected images. Accordingly, there is a need to generate a plurality of aberration-corrected images by executing an aberration correcting process for the entire image taken by the imaging unit. This has an extremely large processing load and is likely to increase the processing time. As a result, this is likely to significantly decrease the measurement efficiency.

SUMMARY

A measurement device according to one or more embodiments improves the measurement accuracy and improves the measurement efficiency.

Embodiments of the present invention are described. Functions and advantageous effects according to one or more embodiments are also described as appropriate.

A measurement device according to one or more embodiments comprises: a predetermined optical system configured to split predetermined incident light into two lights, to radiate one of the two lights as measurement light to a measurement object and the other of the two lights as reference light to a reference surface, and to recombine the two lights to combined light and emit the combined light; an irradiation unit configured to emit predetermined light that is made to enter the predetermined optical system; an imaging unit configured to take an image of output light that is emitted from the predetermined optical system; and an image processor configured to perform measurement with regard to a predetermined measurement area of the measurement object, based on an interference fringe image taken and obtained by the imaging unit.

The image processor comprises a first data obtaining unit configured to obtain a plurality of complex amplitude data at a predetermined position in an optical axis direction at predetermined intervals in at least a predetermined range in the optical axis direction, with regard to a specific area that is a part set in advance in the measurement area, based on the interference fringe image taken and obtained by the imaging unit; an image acquisition unit configured to obtain a plurality of intensity images at the predetermined intervals with regard to the specific area, from the plurality of complex amplitude data at the predetermined intervals with regard to the specific area obtained by the first data obtaining unit; a position determining unit configured to determine the predetermined position in the optical axis direction, based on the plurality of intensity images obtained by the image acquisition unit; a second data obtaining unit configured to obtain complex amplitude data at the position determined by the position determining unit with regard to the entire measurement area; and a measurement execution unit configured to perform measurement with regard to the measurement area, based on the complex amplitude data obtained by the second data obtaining unit.

The "predetermined optical system" includes not only "an optical system that causes interference of reference light and measurement light inside thereof and outputs the reference light and the measurement light as interfering lights" but "an optical system that outputs reference light and measurement light as simple combined light without causing interference of the reference light and the measurement light inside thereof". When the "output light" output from the "predetermined optical system" is "combined light", the combined light is to be converted into "interfering light" by means of a predetermined interfering unit in a stage at least prior to imaging by the "imaging unit", in order to take "interference fringe images".

Accordingly, an optical system configured to split predetermined incident light into two lights, to radiate one of the lights as measurement light to a measurement object and the other of the lights as reference light to a reference surface, and to recombine the two lights to combined light and emit the combined light for the purpose of causing interference of lights (taking interference fringe images) may be called "interference optical system". Accordingly, in one or more embodiments, the "predetermined optical system (specific optical system)" may be regarded as "interference optical system."

The measurement device of one or more embodiments obtains complex amplitude data at a plurality of positions in the optical axis direction not with regard to the entire measurement area but with regard to only the specific area (limited narrow range) that is a part set in advance in the measurement area, and searches for and determines a focused optimum position in the measurement object (specific area), based on the obtained complex amplitude data. The measurement device of one or more embodiments subsequently obtains complex amplitude data at the determined position with regard to the entire measurement area and performs measurement with regard to the measurement area.

This configuration reduces the processing load for obtaining data required for measurement of the measurement area and shortens the time period required for such processing. As a result, this improves the measurement accuracy and improves the measurement efficiency.

The above "predetermined interval" may be, for example, a "focusing range" in the optical axis direction or an interval of "a measurement range".

In the measurement device according to one or more embodiments, the position determining unit may determine a position of the specific area in the optical axis direction, based on the plurality of intensity images obtained by the image acquisition unit.

The measurement device of one or more embodiments is configured to specify the position in the optical axis direction (position in the height direction) of the measurement object (specific area), obtain complex amplitude data of the entire measurement area at the specified position and perform measurement. This configuration can obtain the optimum data of the higher accuracy focused on the measurement object (specific area), compared with a configuration that simply extracts optimum data among a plurality of different complex amplitude data obtained at predetermined intervals. As a result, this configuration further improves the measurement accuracy.

In the measurement device according to one or more embodiments, the specific area may be an area used as a basis for measurement in the optical axis direction with regard to the measurement area.

The measurement device of one or more embodiments allows for measurement under the optimum data of the higher accuracy focused on the specific area as the measurement basis. This configuration further improves the measurement accuracy.

In the measurement device according to one or more embodiments, the specific area is set at a plurality of positions.

The measurement device of one or more embodiments sets the plurality of specific areas and thereby enables the optimum position where the complex amplitude data of the entire measurement area are to be obtained, to be found more readily.

When the measurement area has a height difference due to, for example, warp or inclination of the measurement object, setting only one specific area is likely to fail to obtain data focused on the entire measurement area.

The configuration of one or more embodiments, on the other hand, sets the plurality of specific areas and executes the series of processing according to one or more embodiments with regard to each of the plurality of specific areas. This configuration can thus obtain data focused on the entire measurement area as a whole. The data focused on the entire measurement area may be obtained, for example, by using data at a first position in the optical axis direction for a first area included in the measurement area and using data at a second position in the optical axis direction for a second area.

The measurement device according to one or more embodiments may further comprise a phase shift unit configured to produce a relative phase difference between the reference light and the measurement light. The image processor may be configured to perform measurement with regard to the predetermined measurement area of the measurement object, based on a plurality of interference fringe images obtained by the imaging unit that takes images of the output light having a phase shifted by a plurality of times by the phase shift unit.

In the measurement device according to one or more embodiments, the irradiation unit may comprise a first irradiation unit configured to emit first light that includes polarized light of a first wavelength and that is made to enter the predetermined optical system; and a second irradiation unit configured to emit second light that includes polarized light of a second wavelength and that is made to enter the predetermined optical system. The imaging unit may comprise a first imaging unit configured to take an image of output light with regard to the first light that is emitted from the predetermined optical system when the first light enters the predetermined optical system; and a second imaging unit configured to take an image of output light with regard to the second light that is emitted from the predetermined optical system when the second light enters the predetermined optical system.

Using the two different types of lights having different wavelengths like one or more embodiments expands the measurement range. This configuration accordingly reduces the processing load when the first data obtaining unit obtains complex amplitude data with regard to the specific area at the intervals of the measurement range.

The "first light" radiated from the "first irradiation unit" needs to be light including at least "polarized light of a first wavelength (first polarized light)" and may be light including other extra components (for example, "non-polarized light" and "circularly polarized light") that are subsequently cut by the "predetermined optical system".

Similarly, the "second light" radiated from the "second irradiation unit" needs to be light including at least "polarized light of a second wavelength (second polarized light)" and may be light including other extra components (for example, "non-polarized light" and "circularly polarized light") that are subsequently cut by the "predetermined optical system".

The "output light with regard to the first light" output from the "predetermined optical system (specific optical system)" includes "combined light of reference light and measurement light with regard to the first light or interfering light produced by interfering the combined light". The "output light with regard to the second light" includes "combined light of reference light and measurement light with regard to the second light or interfering light produced by interfering the combined light".

In the measurement device according to one or more embodiments, the measurement object may be a wafer substrate with a bump formed thereon.

The measurement device of one or more embodiments allows for measurement of bumps formed on the wafer substrate. In bump inspection, the good/poor quality of the bump may be determined, based on the measurement value. The bump inspection accordingly has the functions and the advantageous effects of one or more embodiments and ensures the good/poor quality determination with high accuracy. As a result, this configuration improves the inspection accuracy and the inspection efficiency using a bump inspection device.

DETAILED DESCRIPTION OF EMBODIMENTS

Figure 1:
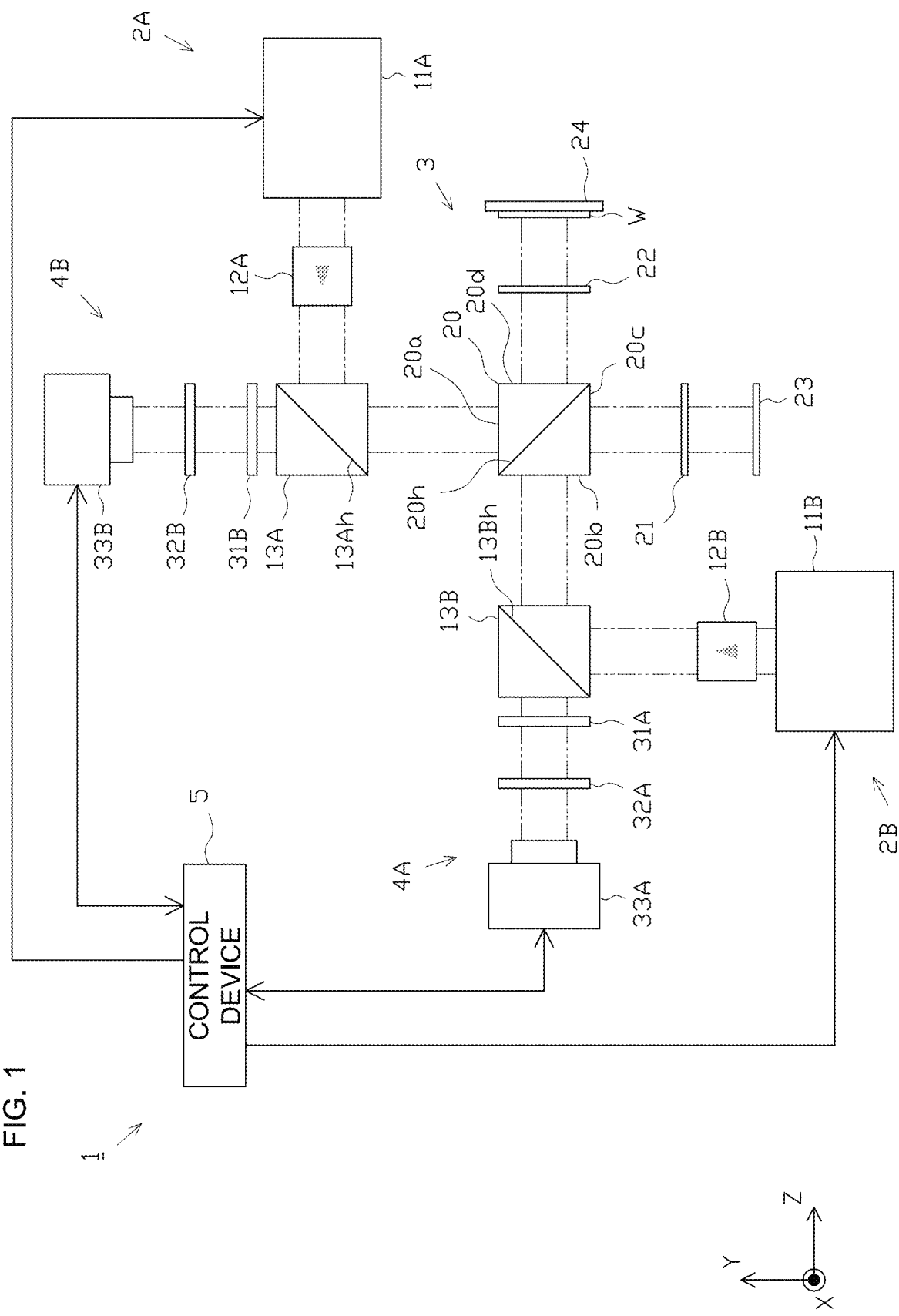
FIG. 1 is a schematic configuration diagram illustrating a measurement device according to one or more embodiments.
Figure 2:
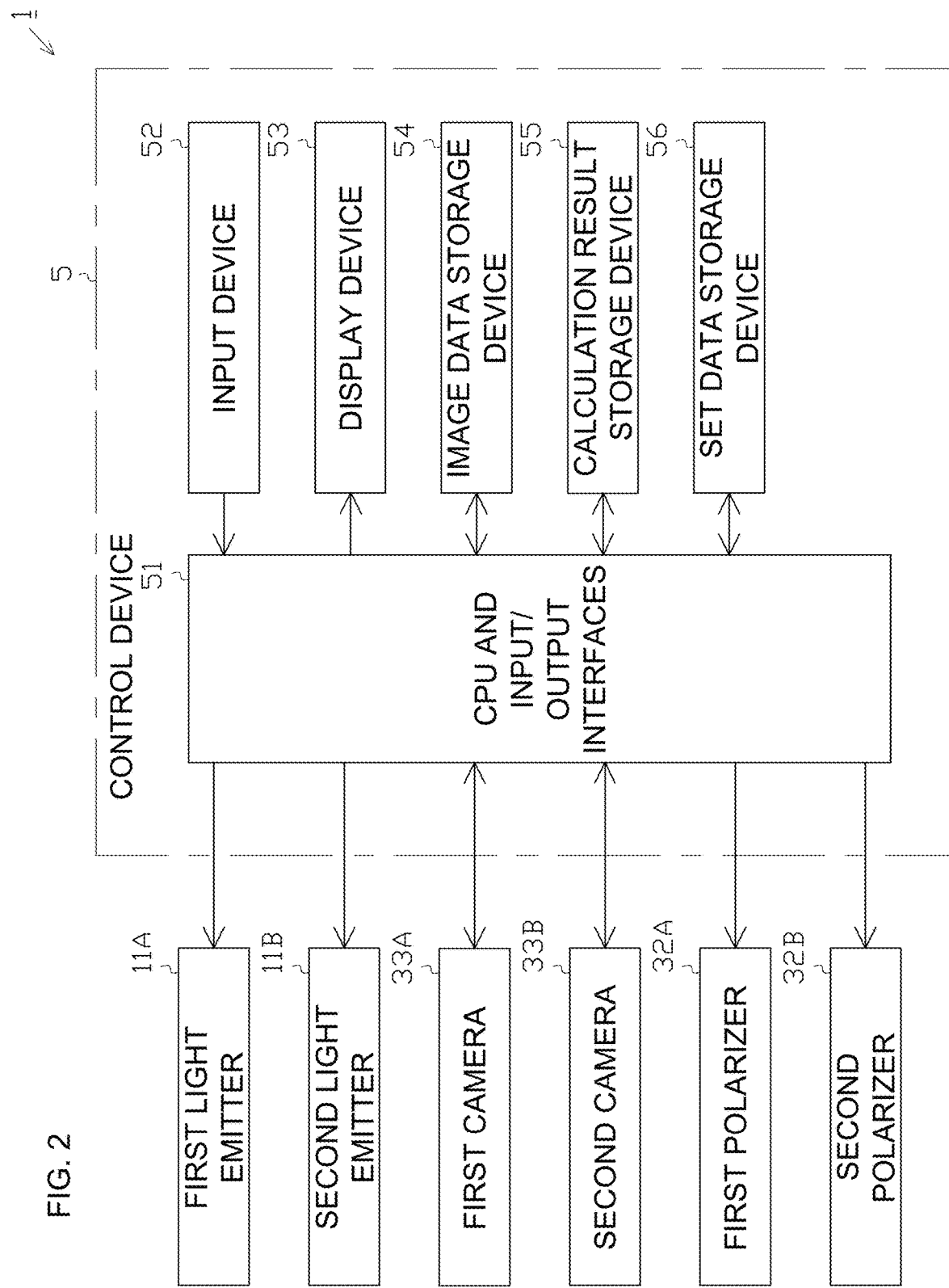
FIG. 2 is a block diagram illustrating the electrical configuration of the measurement device according to one or more embodiments.

The following describes embodiments of a measurement device with reference to the drawings. FIG. 1 is a diagram illustrating the schematic configuration of a measurement device 1 according to one or more embodiments. FIG. 2 is a block diagram illustrating the electrical configuration of the measurement device 1. In the description below, as a matter of convenience, a front-rear direction of the sheet surface of FIG. 1 is called "X-axis direction", a top-bottom direction of the sheet surface is called "Y-axis direction" and a left-right direction of the sheet surface is called "Z-axis direction".

The measurement device 1 is configured based on the principle of the Michelson interferometer and includes two projection optical systems 2A and 2B (first projection optical system 2A and second projection optical system 2B) serving as irradiators to emit lights of specific wavelengths, an interference optical system 3 configured such that the lights respectively emitted from the projection optical systems 2A and 2B enter, two imaging systems 4A and 4B (first imaging system 4A and second imaging system 4B) serving as imaging units to take images of the lights emitted from the interference optical system 3, and a control device 5 configured to execute various controls, image processing, calculations and the like involved in the projection optical systems 2A and 2B, the interference optical system 3, the imaging systems 4A and 4B and the like.

The "control device 5" is configured as the "image processor (processor)" according to one or more embodiments, and the "interference optical system 3" is configured as the "predetermined optical system (specific optical system)" according to one or more embodiments. In one or more embodiments, the "interference optical system" denotes an optical system configured to split a predetermined incident light into two lights (measurement light and reference light), provide the two lights with an optical path difference, recombine the two lights and output the combined light, for the purpose of causing interference of light (taking an interference fringe image). In other words, the "interference optical system" is not limited to an optical system that internally causes interference of two lights and outputs the interfering light but may also be an optical system that simply combines two lights and outputs the combined light without internally causing interference of two lights. Accordingly, as described later in one or more embodiments, when two lights (measurement light and reference light) are output as the combined light without interference from the "interference optical system", interfering light is obtained by means of a predetermined interfering unit in a stage at least prior to imaging (for example, inside of the imaging system).

The following describes the configuration of the two projection optical systems 2A and 2B (first projection optical system 2A and second projection optical system 2B) in detail. The first projection optical system 2A includes, for example, a first light emitter 11A, a first light isolator 12A and a first non-polarizing beam splitter 13A. The "first light emitter 11A" is configured as the "first irradiation unit" according to one or more embodiments.

Although not being illustrated, the first light emitter 11A includes, for example, a laser light source configured to output linearly polarized light of a specific wavelength $\lambda_1$, a beam expander configured to expand the linearly polarized light output from the laser light source and emit the expanded light as parallel light, a polarizer configured to adjust the intensity, and a half wave plate configured to adjust the polarizing direction.

Under the configuration described above, according to one or more embodiments, the first light emitter 11A emits, leftward in the Z-axis direction, linearly polarized light of a wavelength $\lambda_1$ (for example, $\lambda_1$=1500 nm) having a polarizing direction that is a direction inclined at 45 degrees to the X-axis direction and the Y-axis direction. The "wavelength $\lambda_1$" corresponds to the "first wavelength" according to one or more embodiments. In the description below, the light of the wavelength $\lambda_1$ emitted from the first light emitter 11A is called "first light".

The first light isolator 12A is an optical element configured to transmit only a light traveling in one direction (leftward in the Z-axis direction according to one or more embodiments) but block a light traveling in a reverse direction (rightward in the Z-axis direction according to one or more embodiments). This configuration allows for transmission of only the first light emitted from the first light emitter 11A and thereby prevents damage and destabilization of the first light emitter 11A due to return light.

The first non-polarizing beam splitter 13A is a cube-shaped known optical member configured by joining right angle prisms (triangular prisms having an isosceles right triangular bottom surface: the same applies hereinafter) together to be integrated, and its joint surface 13Ah is coated with, for example, a metal film. The "first non-polarizing beam splitter 13A" is configured as the "first light guiding unit" according to one or more embodiments.

The non-polarizing beam splitter is configured to split incident light including polarization state into transmitted light and reflected light at a predetermined ratio. The same applies hereinafter. According to one or more embodiments, a half mirror having a 1:1 split ratio is employed as the non-polarizing beam splitter. The half mirror splits the incident light to provide a P-polarized light component and an S-polarized light component of the transmitted light and a P-polarized light component and an S-polarized light component of the reflected light all at identical rates and provide the respective polarization states of the transmitted light and the reflected light that are identical with the polarization state of the incident light.

According to one or more embodiments, linearly polarized light having a polarizing direction that is a direction parallel to the sheet surface of FIG. 1 (Y-axis direction or Z-axis direction) is called P-polarized light (P-polarized light component). Linearly polarized light having a polarizing direction that is the X-axis direction perpendicular to the sheet surface of FIG. 1 is called S-polarized light (S-polarized light component).

The first non-polarizing beam splitter 13A is arranged such that one of two surfaces adjoining to each other across the joint surface 13Ah is perpendicular to the Y-axis direction and the other of the two surfaces is perpendicular to the Z-axis direction. In other words, the joint surface 13Ah of the first non-polarizing beam splitter 13A is arranged to be inclined at 45 degrees to the Y-axis direction and the Z-axis direction. More specifically, the first non-polarizing beam splitter 13A is arranged to transmit part (half) of the first light that enters leftward in the Z-axis direction from the first light emitter 11A via the first light isolator 12A, leftward in the Z-axis direction and reflect the remaining part (remaining half) of the first light downward in the Y-axis direction.

Like the first projection optical system 2A described above, the second projection optical system 2B includes, for example, a second light emitter 11B, a second light isolator 12B and a second non-polarizing beam splitter 13B. The "second light emitter 11B" is configured as the "second irradiation unit" according to one or more embodiments.

Like the first light emitter 11A described above, the second light emitter 11B includes, for example, a laser light source configured to output linearly polarized light of a specific wavelength $\lambda_2$, a beam expander configured to expand the linearly polarized light output from the laser light source and emit the expanded light as parallel light, a polarizer configured to adjust the intensity, and a half wave plate configured to adjust the polarizing direction.

Under the configuration described above, according to one or more embodiments, the second light emitter 11B emits, upward in the Y-axis direction, linearly polarized light of a wavelength $\lambda_2$ (for example, $\lambda_2$=1503 nm) having a polarizing direction that is a direction inclined at 45 degrees to the X-axis direction and the Z-axis direction. The "wavelength $\lambda_2$" corresponds to the "second wavelength" according to one or more embodiments. In the description below, the light of the wavelength $\lambda_2$ emitted from the second light emitter 11B is called "second light".

Like the first light isolator 12A, the second light isolator 12B is an optical element configured to transmit only a light traveling in one direction (upward in the Y-axis direction according to one or more embodiments) but block a light traveling in a reverse direction (downward in the Y-axis direction according to one or more embodiments). This configuration allows for transmission of only the second light emitted from the second light emitter 11B and thereby prevents damage and destabilization of the second light emitter 11B due to return light.

Like the first non-polarizing beam splitter 13A, the second non-polarizing beam splitter 13B is a cube-shaped known optical member configured by joining right angle prisms together to be integrated, and its joint surface 13Bh is coated with, for example, a metal film. The "second non-polarizing beam splitter 13B" is configured as the "second light guiding unit" according to one or more embodiments.

The second non-polarizing beam splitter 13B is arranged such that one of two surfaces adjoining to each other across the joint surface 13Bh is perpendicular to the Y-axis direction and the other of the two surfaces is perpendicular to the Z-axis direction. In other words, the joint surface 13Bh of the second non-polarizing beam splitter 13B is arranged to be inclined at 45 degrees to the Y-axis direction and the Z-axis direction. More specifically, the second non-polarizing beam splitter 13B is arranged to transmit part (half) of the second light that enters upward in the Y-axis direction from the second light emitter 11B via the second light isolator 12B, upward in the Y-axis direction and reflect the remaining part (remaining half) of the second light rightward in the Z-axis direction.

The following describes the configuration of the interference optical system 3. The interference optical system 3 includes, for example, a polarizing beam splitter (PBS) 20, quarter wave plates 21 and 22, a reference surface 23 and a placement structure 24.

The polarizing beam splitter 20 is a cube-shaped known optical member configured by joining right angle prisms together to be integrated, and its joint surface (boundary surface) 20h is coated with, for example, a dielectric multilayer film.

The polarizing beam splitter 20 is configured to split linearly polarized incident light into two polarized light components (P-polarized light component and S-polarized light component) having polarizing directions perpendicular to each other. According to one or more embodiments, the polarizing beam splitter 20 is configured to transmit the P-polarized light component and reflect the S-polarized light component.

The polarizing beam splitter 20 is arranged such that one of two surfaces adjoining to each other across the joint surface 20h is perpendicular to the Y-axis direction and the other of the two surfaces is perpendicular to the Z-axis direction. In other words, the joint surface 20h of the polarizing beam splitter 20 is arranged to be inclined at 45 degrees to the Y-axis direction and the Z-axis direction.

More specifically, a first surface (upper side surface in the Y-axis direction) 20a of the polarizing beam splitter 20, which the first light reflected downward in the Y-axis direction from the above first non-polarizing beam splitter 13A enters, and a third surface (lower side surface in the Y-axis direction) 20c opposed to the first surface 20a are arranged to be perpendicular to the Y-axis direction. The "first surface 20a of the polarizing beam splitter 20" corresponds to the "first input-output element" according to one or more embodiments.

A second surface (left side surface in the Z-axis direction) 20b of the polarizing beam splitter 20, which is a surface adjoining to the first surface 60a across the joint surface 20h and which the second light reflected rightward in the Z-axis direction from the above second non-polarizing beam splitter 13B enters, and a fourth surface (right side surface in the Z-axis direction) 20d opposed to the second surface 20b are arranged to be perpendicular to the Z-axis direction. The "second surface 20b of the polarizing beam splitter 20" corresponds to the "second input-output element" according to one or more embodiments.

The quarter wave plate 21 is arranged to be opposed in the Y-axis direction to the third surface 20c of the polarizing beam splitter 20, and the reference surface 23 is arranged to be opposed in the Y-axis direction to the quarter wave plate 21.

The quarter wave plate 21 serves to convert linearly polarized light into circularly polarized light and to convert circularly polarized light into linearly polarized light. Accordingly, linearly polarized light (reference light) emitted from the third surface 20c of the polarizing beam splitter 20 is converted into circularly polarized light by the quarter wave plate 21 and is radiated to the reference surface 23. The reference light reflected by the reference surface 23 is reconverted from the circularly polarized light into the linearly polarized light by the quarter wave plate 21 and enters the third surface 20c of the polarizing beam splitter 20.

The quarter wave plate 22 is arranged, on the other hand, to be opposed in the Z-axis direction to the fourth surface 20d of the polarizing beam splitter 20, and the placement structure 24 is arranged to be opposed in the Z-axis direction to the quarter wave plate 22.

The quarter wave plate 22 serves to convert linearly polarized light into circularly polarized light and to convert circularly polarized light into linearly polarized light. Accordingly, linearly polarized light (measurement light) emitted from the fourth surface 20d of the polarizing beam splitter 20 is converted into circularly polarized light by the quarter wave plate 22 and is radiated to a work W as a measurement object placed on the placement structure 24. The measurement light reflected by the work W is reconverted from the circularly polarized light into the linearly polarized light by the quarter wave plate 22 and enters the fourth surface 20d of the polarizing beam splitter 20.

The following describes the configuration of the two imaging systems 4A and 4B (first imaging system 4A and second imaging system 4B) in detail. The first imaging system 4A includes a quarter wave plate 31A, a first polarizer 32A and a first camera 33A configured as the first imaging unit.

The quarter wave plate 31A is configured to respectively convert linearly polarized lights that are transmitted through the second non-polarizing beam splitter 13B leftward in the Z direction (reference light component and measurement light component of the first light) into circularly polarized lights.

The first polarizer 32A is configured to cause the respective components of the first light converted into the circularly polarized light by the quarter wave plate 31A to be transmitted selectively. This configuration provides interference of the reference light component and the measurement light component of the first light having different rotating directions with regard to a specific phase. The "first polarizer 32A" is configured as the "phase shift unit" and the "interfering unit" according to one or more embodiments.

The first polarizer 32A according to one or more embodiments is configured to rotate about the Z-axis direction as the axial center and is controlled to change its transmission axis direction by 45 degrees each. More specifically, the first polarizer 32A is controlled to change the transmission axis direction to "0 degree", "45 degrees", "90 degrees" and "135 degrees" relative to the Y-axis direction.

This configuration causes interference of the reference light component and the measurement light component of the first light transmitted through the first polarizer 32A in four different phases. This accordingly generates interfering lights having phases that are different from one another by 90 degrees each. More specifically, this generates an interfering light having a phase of "0 degree", an interfering light having a phase of "90 degrees", an interfering light having a phase of "180 degrees" and an interfering light having a phase of "270 degrees".

The first camera 33A has a known configuration including a lens, an imaging element 33Aa (shown in FIG. 6) and the like. According to one or more embodiments, a CCD area sensor is employed as the imaging element 33Aa of the first camera 33A. The imaging element 33Aa is, however, not limited to one or more embodiments. For example, a CMOS area sensor or the like may be employed as the imaging element 33Aa. A telecentric lens is used as the lens.

Image data taken by the first camera 33A are converted into digital signals inside of the first camera 33A and are input in the form of the digital signals into the control device 5 (image data storage device 54).

More specifically, an interference fringe image having the phase of "0 degree", an interference fringe image having the phase of "90 degrees, an interference fringe image having the phase of "180 degrees", and an interference fringe image having the phase of "270 degrees" with regard to the first light are taken by the first camera 33A.

Like the first imaging system 4A, the second imaging system 4B includes a quarter wave plate 31B, a second polarizer 32B and a second camera 33B configured as the second imaging unit.

The quarter wave plate 31B is configured to respectively convert linearly polarized lights that are transmitted through the first non-polarizing beam splitter 13A upward in the Y direction (reference light component and measurement light component of the second light) into circularly polarized lights.

Like the first polarizer 32A, the second polarizer 32B is configured to cause the respective components of the second light converted into the circularly polarized light by the quarter wave plate 31B to be transmitted selectively. This configuration provides interference of the reference light component and the measurement light component of the second light having different rotating directions with regard to a specific phase. The "second polarizer 32B" is configured as the "phase shift unit" and the "interfering unit" according to one or more embodiments.

The second polarizer 32B according to one or more embodiments is configured to rotate about the Y-axis direction as the axial center and is controlled to change its transmission axis direction by 45 degrees each. More specifically, the second polarizer 32B is controlled to change the transmission axis direction to "0 degree", "45 degrees", "90 degrees" and "135 degrees" relative to the X-axis direction.

This configuration causes interference of the reference light component and the measurement light component of the second light transmitted through the second polarizer 32B in four different phases. This accordingly generates interfering lights having phases that are different from one another by 90 degrees each. More specifically, this generates an interfering light having a phase of "0 degree", an interfering light having a phase of "90 degrees", an interfering light having a phase of "180 degrees" and an interfering light having a phase of "270 degrees".

Like the first camera 33A, the second camera 33B has a known configuration including a lens, an imaging element 33Ba (shown in FIG. 6) and the like. According to one or more embodiments, as in the case of the first camera 33A, a CCD area sensor is employed as the imaging element 33Ba of the second camera 33B. The imaging element 33Ba is, however, not limited to one or more embodiments. For example, a CMOS area sensor or the like may be employed as the imaging element 33Ba. A telecentric lens is used as the lens.

As in the case of the first camera 33A, image data taken by the second camera 33B are converted into digital signals inside of the second camera 33B and are input in the form of the digital signals into the control device 5 (image data storage device 54).

More specifically, an interference fringe image having the phase of "0 degree", an interference fringe image having the phase of "90 degrees, an interference fringe image having the phase of "180 degrees", and an interference fringe image having the phase of "270 degrees" with regard to the second light are taken by the second camera 33B.

The following describes the electrical configuration of the control device 5. As shown in FIG. 2, the control device 5 includes CPU and input/output interfaces 51 configured to control the entire measurement device 1, an input device 52 configured by a keyboard and a mouse or by a touch panel as the "input unit", a display device 53 configured as the "display unit" including a display screen such as a liquid crystal screen, an image data storage device 54 configured to sequentially store the image data and the like taken by the cameras 33A and 33B, a calculation result storage device 55 configured to store results of various calculations, and a set data storage device 56 configured to store various information in advance. These devices 52 to 56 are electrically connected with the CPU and input/output interfaces 51.

The following describes the functions of the measurement device 1. As described later, the configuration of one or more embodiments simultaneously performs radiation of the first light and the second light and causes the optical path of the first light and the optical path of the second light to partly overlap each other. For the better understanding, the optical path of the first light and the optical path of the second light are illustrated in different drawings and are described individually.

Figure 3:
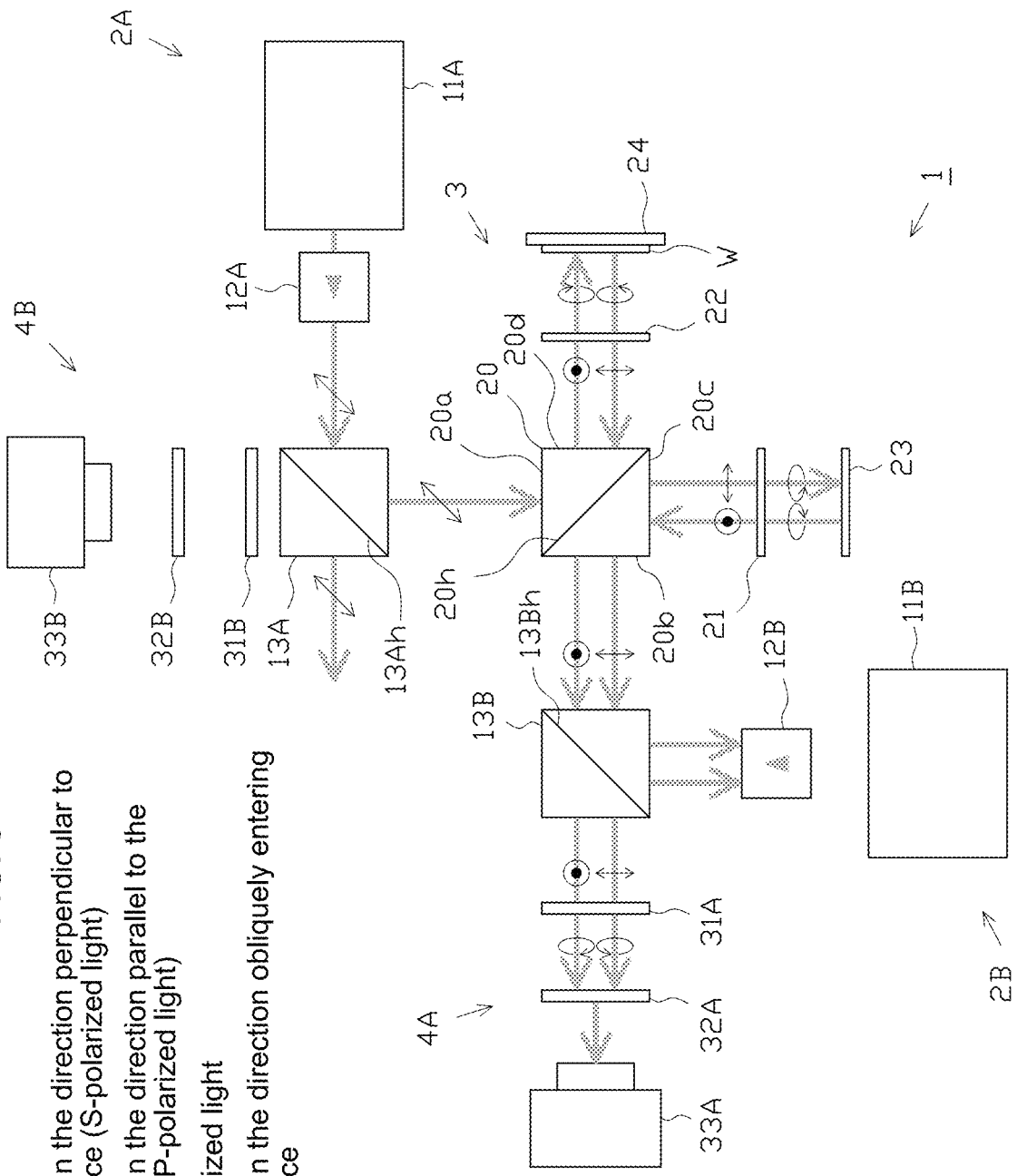
FIG. 3 is an optical path diagram illustrating an optical path of first light according to one or more embodiments.

The optical path of the first light is described first with reference to FIG. 3. As shown in FIG. 3, the first light of the wavelength $\lambda_1$ (linearly polarized light having the polarizing direction that is inclined at 45 degrees to the X-axis direction and the Y-axis direction) is emitted leftward in the Z-axis direction from the first light emitter 11A.

The first light emitted from the first light emitter 11A passes through the first light isolator 12A and enters the first non-polarizing beam splitter 13A. Part of the first light entering the first non-polarizing beam splitter 13A is transmitted leftward in the Z-axis direction, while the remaining part is reflected downward in the Y-axis direction.

The first light reflected downward in the Y-axis direction (linearly polarized light having the polarizing direction that is inclined at 45 degrees to the X-axis direction and the Z-axis direction) enters the first surface 20a of the polarizing beam splitter 20. The first light transmitted leftward in the Z-axis direction, on the other hand, does not enter any optical system or the like but is left as waste light.

This waste light may be used for measurement of the wavelength or for measurement of the light power as appropriate. This stabilizes the light source and thereby improves the measurement accuracy.

With regard to the first light entering the first surface 20a of the polarizing beam splitter 20 downward in the Y-axis direction, its P-polarized light component is transmitted downward in the Y-axis direction and is emitted from the third surface 20c as reference light, whereas its S-polarized light component is reflected rightward in the Z-axis direction and is emitted from the fourth surface 20d as measurement light.

The reference light (P-polarized light) with regard to the first light emitted from the third surface 20c of the polarizing beam splitter 20 passes through the quarter wave plate 21 to be converted into clockwise circularly polarized light and is then reflected by the reference surface 23. In this process, the rotating direction relative to the traveling direction of light is maintained. The reference light with regard to the first light subsequently passes through the quarter wave plate 21 again to be converted from the clockwise circularly polarized light into S-polarized light and reenters the third surface 20c of the polarizing beam splitter 20.

The measurement light (S-polarized light) with regard to the first light emitted from the fourth surface 20d of the polarizing beam splitter 20, on the other hand, passes through the quarter wave plate 22 to be converted into counterclockwise circularly polarized light and is then reflected by the work W. In this process, the rotating direction relative to the traveling direction of light is maintained. The measurement light with regard to the first light subsequently passes through the quarter wave plate 22 again to be converted from the counterclockwise circularly polarized light into P-polarized light and then reenters the fourth surface 20d of the polarizing beam splitter 20.

The reference light (S-polarized light) with regard to the first light reentering the third surface 20c of the polarizing beam splitter 20 is reflected by the joint surface 20h leftward in the Z-axis direction, while the measurement light (P-polarized light) with regard to the first light reentering the fourth surface 20d is transmitted through the joint surface 20h leftward in the Z-axis direction. The combined light generated by combining the reference light and the measurement light with regard to the first light is then emitted as the output light from the second surface 20b of the polarizing beam splitter 20.

The combined light (reference light and measurement light) with regard to the first light emitted from the second surface 20b of the polarizing beam splitter 20 enters the second non-polarizing beam splitter 13B. Part of the combined light with regard to the first light entering the second non-polarizing beam splitter 13B leftward in the Z-axis direction is transmitted leftward in the Z-axis direction, while the remaining part is reflected downward in the Y-axis direction. The combined light (reference light and measurement light) transmitted leftward in the Z-axis direction enters the first imaging system 4A. The combined light reflected downward in the Y-axis direction, on the other hand, is blocked by the second light isolator 12B to be left as waste light.

When the combined light (reference light and measurement light) with regard to the first light enters the first imaging system 4A, the quarter wave plate 31A converts its reference light component (S-polarized light component) into counterclockwise circularly polarized light, while converting its measurement light component (P-polarized light component) into clockwise circularly polarized light. The counterclockwise circularly polarized light and the clockwise circularly polarized light have different rotating directions and accordingly do not interfere with each other.

When the combined light with regard to the first light subsequently passes through the first polarizer 32A, its reference light component and its measurement light component interfere with each other in a phase according to the angle of the first polarizer 32A. An image of the interfering light with regard to the first light is then taken by the first camera 33A.

Figure 4:
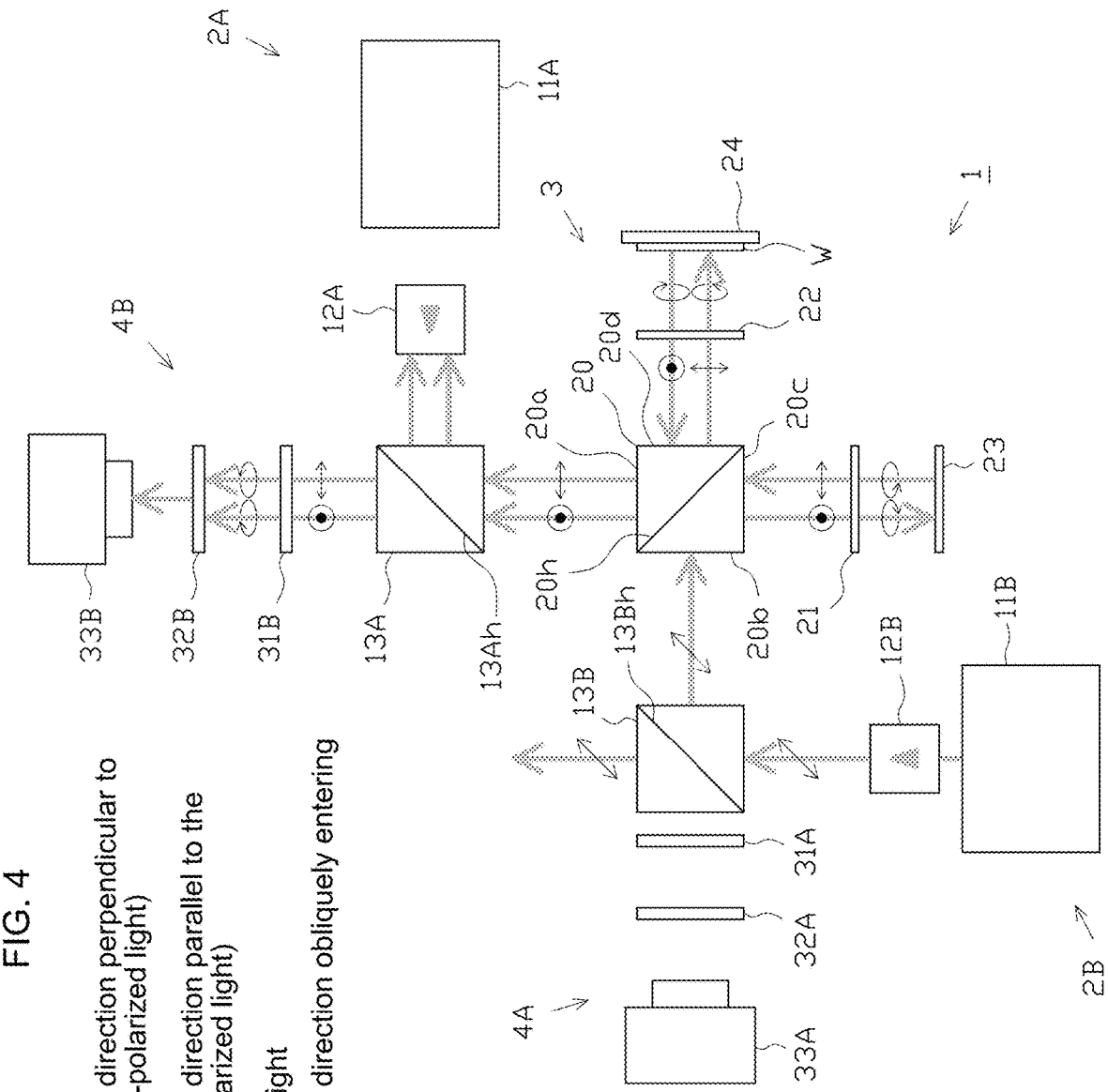
FIG. 4 is an optical path diagram illustrating an optical path of second light according to one or more embodiments.

The optical path of the second light is described next with reference to FIG. 4. As shown in FIG. 4, the second light of the wavelength $\lambda_2$ (linearly polarized light having the polarizing direction that is inclined at 45 degrees to the X-axis direction and the Z-axis direction) is emitted upward in the Y-axis direction from the second light emitter 11B.

The second light emitted from the second light emitter 11B passes through the second light isolator 12B and enters the second non-polarizing beam splitter 13B. Part of the second light entering the second non-polarizing beam splitter 13B is transmitted upward in the Y-axis direction, while the remaining part is reflected rightward in the Z-axis direction.

The second light reflected rightward in the Z-axis direction (linearly polarized light having the polarizing direction that is inclined at 45 degrees to the X-axis direction and the Y-axis direction) enters the second surface 20b of the polarizing beam splitter 20. The second light transmitted upward in the Y-axis direction, on the other hand, does not enter any optical system or the like but is left as waste light.

This waste light may be used for measurement of the wavelength or for measurement of the light power as appropriate. This stabilizes the light source and thereby improves the measurement accuracy.

With regard to the second light entering the second surface 20b of the polarizing beam splitter 20 rightward in the Z-axis direction, its S-polarized light component is reflected downward in the Y-axis direction and is emitted from the third surface 20c as reference light, whereas its P-polarized light component is transmitted rightward in the Z-axis direction and is emitted from the fourth surface 20d as measurement light.

The reference light (S-polarized light) with regard to the second light emitted from the third surface 20c of the polarizing beam splitter 20 passes through the quarter wave plate 21 to be converted into counterclockwise circularly polarized light and is then reflected by the reference surface 23. In this process, the rotating direction relative to the traveling direction of light is maintained. The reference light with regard to the second light subsequently passes through the quarter wave plate 21 again to be converted from the counterclockwise circularly polarized light into P-polarized light and reenters the third surface 20c of the polarizing beam splitter 20.

The measurement light (P-polarized light) with regard to the second light emitted from the fourth surface 20d of the polarizing beam splitter 20, on the other hand, passes through the quarter wave plate 22 to be converted into clockwise circularly polarized light and is then reflected by the work W. In this process, the rotating direction relative to the traveling direction of light is maintained. The measurement light with regard to the second light subsequently passes through the quarter wave plate 22 again to be converted from the clockwise circularly polarized light into S-polarized light and then reenters the fourth surface 20d of the polarizing beam splitter 20.

The reference light (P-polarized light) with regard to the second light reentering the third surface 20c of the polarizing beam splitter 20 is transmitted through the joint surface 20h upward in the Y-axis direction, while the measurement light (S-polarized light) with regard to the second light reentering the fourth surface 20d is reflected by the joint surface 20h upward in the Y-axis direction. The combined light generated by combining the reference light and the measurement light with regard to the second light is then emitted as the output light from the first surface 20a of the polarizing beam splitter 20.

The combined light (reference light and measurement light) with regard to the second light emitted from the first surface 20a of the polarizing beam splitter 20 enters the first non-polarizing beam splitter 13A. Part of the combined light with regard to the second light entering the first non-polarizing beam splitter 13A upward in the Y-axis direction is transmitted upward in the Y-axis direction, while the remaining part is reflected rightward in the Z-axis direction. The combined light (reference light and measurement light) transmitted upward in the Y-axis direction enters the second imaging system 4B. The combined light reflected rightward the Z-axis direction, on the other hand, is blocked by the first light isolator 12A to be left as waste light.

When the combined light (reference light and measurement light) with regard to the second light enters the second imaging system 4B, the quarter wave plate 31B converts its reference light component (P-polarized light component) into clockwise circularly polarized light, while converting its measurement light component (S-polarized light component) into counterclockwise circularly polarized light. The counterclockwise circularly polarized light and the clockwise circularly polarized light have different rotating directions and accordingly do not interfere with each other.

When the combined light with regard to the second light subsequently passes through the second polarizer 32B, its reference light component and its measurement light component interfere with each other in a phase according to the angle of the second polarizer 32B. An image of the interfering light with regard to the second light is then taken by the second camera 33B.

Figure 5:
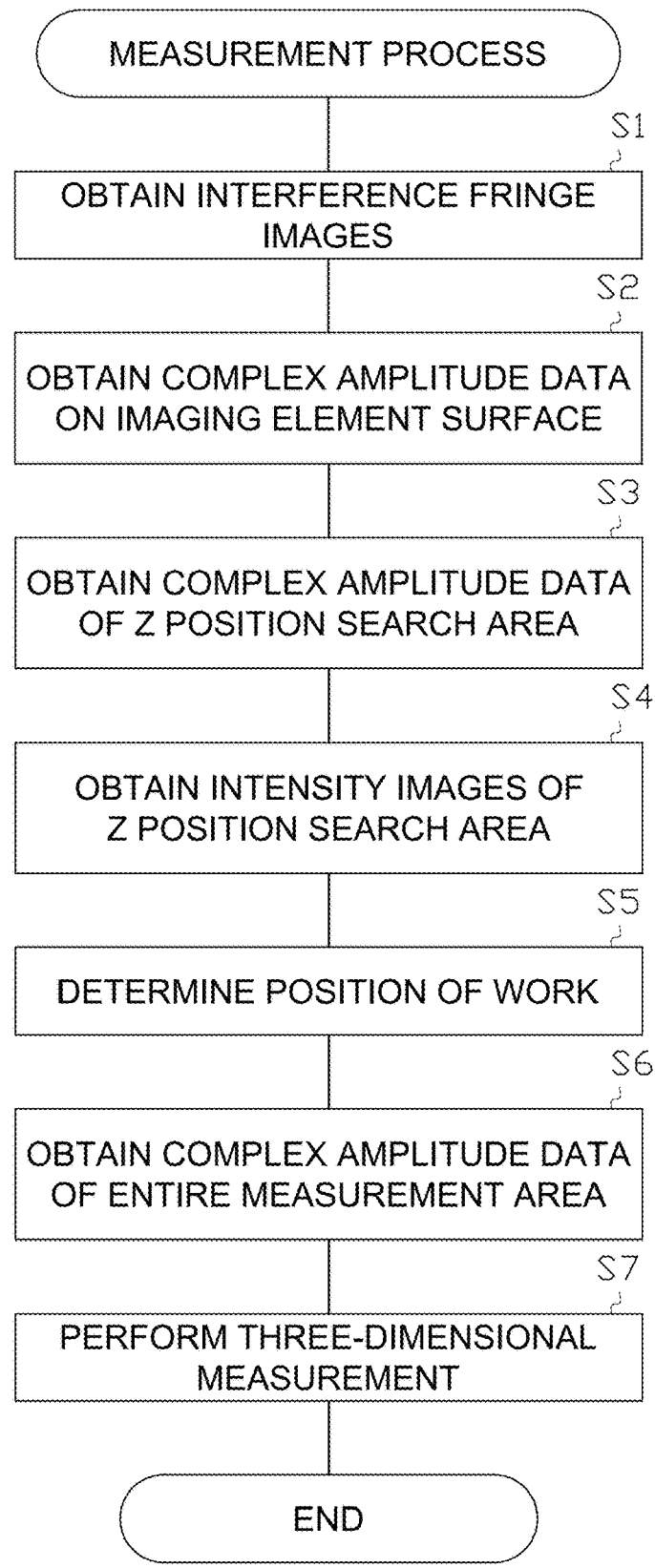
FIG. 5 is a flowchart showing a flow of measurement process according to one or more embodiments.

The following describes in detail a procedure of measurement process executed by the control device 5 with reference to the flowchart of FIG. 5 and the like. In the following description of the measurement process, the imaging element 33Aa-surface of the first camera 33A or the imaging element 33Ba-surface of the second camera 33B is specified as x-y plane, and an optical axis direction perpendicular to the x-y plane is specified as z direction. This coordinate system (x, y, z) is a different coordinate system from the coordinate system (X, Y, Z) used to describe the enter measurement device 1.

At step S1, the control device 5 executes a process of obtaining interference fringe images with regard to a predetermined measurement area of the work W. According to one or more embodiments, the control device 5 obtains four different interference fringe images of different phases with regard to the first light and four different interference fringe images of different phases with regard to the second light. The following describes this process in detail.

After the work W is placed on the placement structure 24, the control device 5 sets the transmission axis direction of the first polarizer 32A of the first imaging system 4A at a predetermined reference position (for example, "0 degree"), and sets the transmission axis direction of the second polarizer 32B of the second imaging system 4B at a predetermined reference position (for example, "0 degree").

The control device 5 subsequently causes the first light to be radiated from the first projection optical system 2A, and simultaneously causes the second light to be radiated from the second projection optical system 2B. As a result, the combined light (reference light and measurement light) with regard to the first light is emitted from the second surface 20b of the polarizing beam splitter 20 of the interference optical system 3, and simultaneously the combined light (reference light and measurement light) with regard to the second light is emitted from the first surface 20a of the polarizing beam splitter 20.

An image of the combined light with regard to the first light emitted from the second surface 20b of the polarizing beam splitter 20 is taken by the first imaging system 4A, and simultaneously an image of the combined light with regard to the second light emitted from the first surface 20a of the polarizing beam splitter 20 is taken by the second imaging system 4B.

The transmission axis directions of the first polarizer 32A and the second polarizer 32B are respectively set to "0 degree". Accordingly, the first camera 33A takes an interference fringe image having the phase of "0 degree" with regard to the first light, and the second camera 33B takes an interference fringe image having the phase of "0 degree" with regard to the second light.

Image data taken by the respective cameras 33A and 33B are output to the control device 5. The control device 5 stores the input image data into the image data storage device 54.

The control device 5 subsequently executes a changeover process of the first polarizer 32A of the first imaging system 4A and the second polarizer 32B of the second imaging system 4B. More specifically, the control device 5 rotates and shifts the first polarizer 32A and the second polarizer 32B to respective positions having the transmission axis direction of "45 degrees".

On completion of the changeover process, the control device 5 executes a second imaging process that is similar to the series of the first imaging process described above. More specifically, the control device 5 causes the first light to be radiated from the first projection optical system 2A, and simultaneously causes the second light to be radiated from the second projection optical system 2B. An image of the combined light with regard to the first light emitted from the second surface 20b of the polarizing beam splitter 20 is taken by the first imaging system 4A, and simultaneously an image of the combined light with regard to the second light emitted from the first surface 20a of the polarizing beam splitter 20 is taken by the second imaging system 4B. The control device 5 accordingly obtains an interference fringe image having the phase of "90 degrees" with regard to the first light and obtains an interference fringe image having the phase of "90 degrees" with regard to the second light.

Two more imaging processes are subsequently executed similarly to the first imaging process and the second imaging process described above. More specifically, a third imaging process is executed with setting the transmission axis directions of the first polarizer 32A and the second polarizer 32B at "90 degrees". The control device 5 accordingly obtains an interference fringe image having the phase of "180 degrees" with regard to the first light and obtains an interference fringe image having the phase of "180 degrees" with regard to the second light.

A fourth imaging process is then executed with setting the transmission axis directions of the first polarizer 32A and the second polarizer 32B at "135 degrees". The control device 5 accordingly obtains an interference fringe image having the phase of "270 degrees" with regard to the first light and obtains an interference fringe image having the phase of "270 degrees" with regard to the second light.

By executing the four imaging processes as described above, the control device 5 obtains all image data required for measurement of the predetermined measurement area on the work W (a total of eight interference fringe images including four different interference fringe images with regard to the first light and four different interference fringe images with regard to the second light).

At subsequent step S2, the control device 5 executes a process of obtaining complex amplitude data Eo(x,y) of light on the imaging element 33Aa-surface and on the imaging element 33Ba-surface. More specifically, the control device 5 obtains complex amplitude data Eo(x,y) of light on the imaging element 33Aa-surface and on the imaging element 33Ba-surface with regard to the first light and the second light, based on the four different interference fringe images with regard to the first light and the four different interference fringe images with regard to the second light.

Interference fringe intensities of the four different interference fringe images with regard to the first light or with regard to the second light at an identical coordinate position (x,y), i.e., luminance values $I_1(x,y)$, $I_2(x,y)$, $I_3(x,y)$ and $I_4(x,y)$, are expressed by relational expressions of [Math. 1] given below:

$$I_1(x,y)=B(x,y)+A(x,y)\cos[\Delta\phi(x,y)]$$

$$I_2(x,y)=B(x,y)+A(x,y)\cos[\Delta\phi(x,y)+90°]$$

$$I_3(x,y)=B(x,y)+A(x,y)\cos[\Delta\phi(x,y)+180°]$$

$$I_4(x,y)=B(x,y)+A(x,y)\cos[\Delta\phi(x,y)+270°] \qquad \text{[Math. 1]}$$

Herein $\Delta\phi(x,y)$ denotes a phase difference based on the optical path difference between the measurement light and the reference light at the coordinates (x,y). A(x,y) denotes an amplitude of the interfering light, and B(x,y) denotes a bias. The reference light is, however, uniform. From this point of view, $\Delta\phi(x,y)$ denotes a "phase of the measurement light", and A(x,y) denotes an "amplitude of the measurement light".

Accordingly, the phase $\Delta\phi(x,y)$ of the measurement light that reaches the imaging element 33Aa-surface or the imaging element 33Ba-surface is determined by a relational expression of [Math. 2] given below, based on the relational expressions of [Math. 1] given above:

$$\Delta\phi(x,y) = \arctan\frac{I_4(x,y) - I_2(x,y)}{I_1(x,y) - I_3(x,y)} \qquad \text{[Math. 2]}$$

The amplitude A(x,y) of the measurement light that reaches the imaging element 33Aa-surface or the imaging element 33Ba-surface is determined by a relational expression of [Math. 3] given below, based on the relational expressions of [Math. 1] given above:

$$A(x,y) = \frac{1}{2} \times \sqrt{\{I_1(x,y) - I_3(x,y)\}^2 + \{I_4(x,y) - I_2(x,y)\}^2} \qquad \text{[Math. 3]}$$

The complex amplitude data Eo(x,y) on the imaging element 33Aa-surface and on the imaging element 33Ba-surface are then calculated from the above phase $\Delta\phi(x,y)$ and amplitude A(x,y) according to a relational expression of [Math. 4] given below, where i denotes an imaginary unit.

$$E_0(x,y)=A(x,y)e^{i\phi(x,y)} \qquad \text{[Math. 4]}$$

At subsequent step S3, the control device 5 executes a process of obtaining complex amplitude data at a plurality of positions in the z direction in a partial specific area set in advance in the predetermined measurement area of the work W. The first data obtaining unit is configured by the function of executing the series of processing involved in steps S2 and S3 described above according to one or more embodiments.

Figure 7:
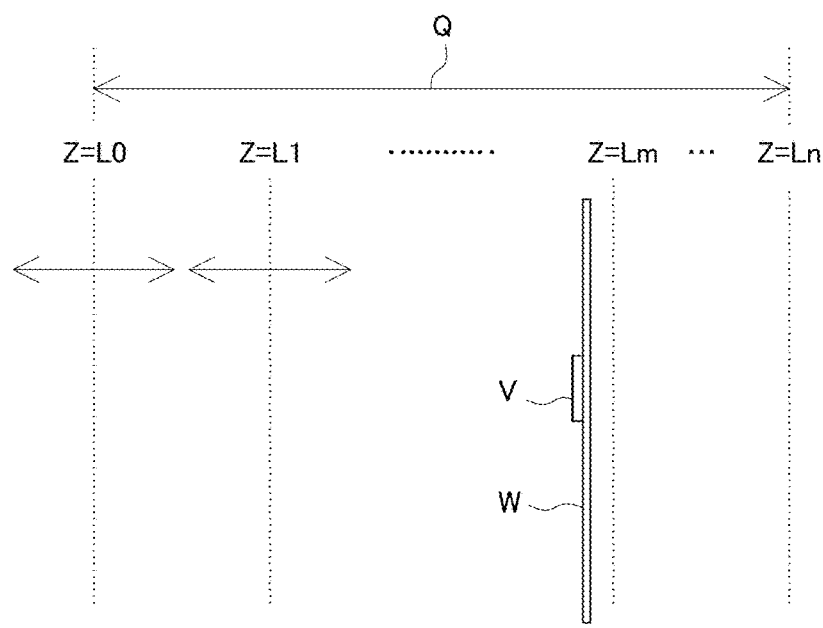
FIG. 7 is a diagram illustrating the positional relationship between the work and the imaging element and the like according to one or more embodiments.
Figure 8:
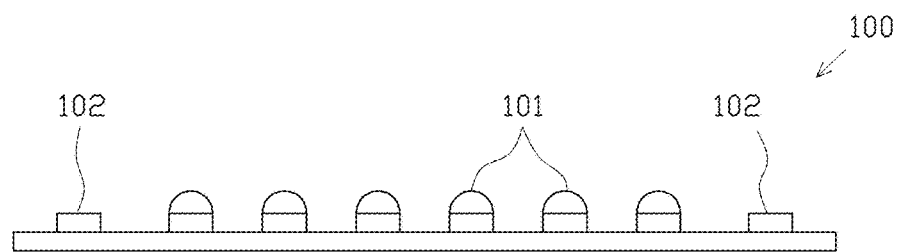
FIG. 8 is a side view diagram illustrating a wafer substrate with bumps formed thereon according to one or more embodiments.

The "specific area" denotes an area set arbitrarily to search for the position of the work W in the z direction in advance. In the description below, the "specific area" is called "z position search area V" (as shown in FIG. 7). For example, when the work W is a wafer substrate 100 as shown in FIG. 8, a patterned part 102 that may be specified as a reference surface for measurement of bumps 101 may be set as the z position search area V.

The following describes the processing of step S3 in detail. A method of obtaining unknown complex amplitude data at different positions in the z direction from known complex amplitude data at a predetermined position in the z direction is described first.

There are provided two coordinate systems (x-y coordinate system and ξ-η coordinate system) that are away from each other by a distance d in the z direction. A relationship shown by [Math. 5] given below is provided, where z=0 in the x-y coordinate system, Eo(x,y) denotes known complex amplitude data of light in the x-y coordinate system, and Eo(ξ,η) denotes unknown complex amplitude data of light in a ξ-η plane that is away from an x-y plane by the distance d. Herein λ denotes wavelength.

$$E_0(x, y) =$$ [Math. 5]

$$\frac{i}{\lambda}\int_{-\infty}^{\infty}\int_{-\infty}^{\infty} E_0(\xi, \eta) \frac{\exp\left(-i\frac{2\pi}{\lambda}\sqrt{d^2 + (\xi - x)^2 + (\eta - y)^2}\right)}{\sqrt{d^2 + (\xi - x)^2 + (\eta - y)^2}} d\xi d\eta =$$

$$\mathcal{F}^{-1}\{\mathcal{F}(E_0(\xi, \eta)) \cdot \mathcal{F}(g(\xi, \eta, x, y))\}$$

$$g(\xi, \eta, x, y) = \frac{i}{\lambda} \frac{\exp\left(-i\frac{2\pi}{\lambda}\sqrt{d^2 + (\xi - x)^2 + (\eta - y)^2}\right)}{\sqrt{d^2 + (\xi - x)^2 + (\eta - y)^2}}$$

$\mathcal{F}$: Fourier Transform $\mathcal{F}^{-1}$: Inverse Fourier Transform

[Math. 6] given below is obtained by solving this expression with respect to Eo(ξ,η):

$$E_0(\xi, \eta) = \mathcal{F}^{-1}\left\{\frac{\mathcal{F}(E_0(x, y))}{\mathcal{F}(g(\xi, \eta, x, y))}\right\}$$ [Math. 6]

Figure 6:
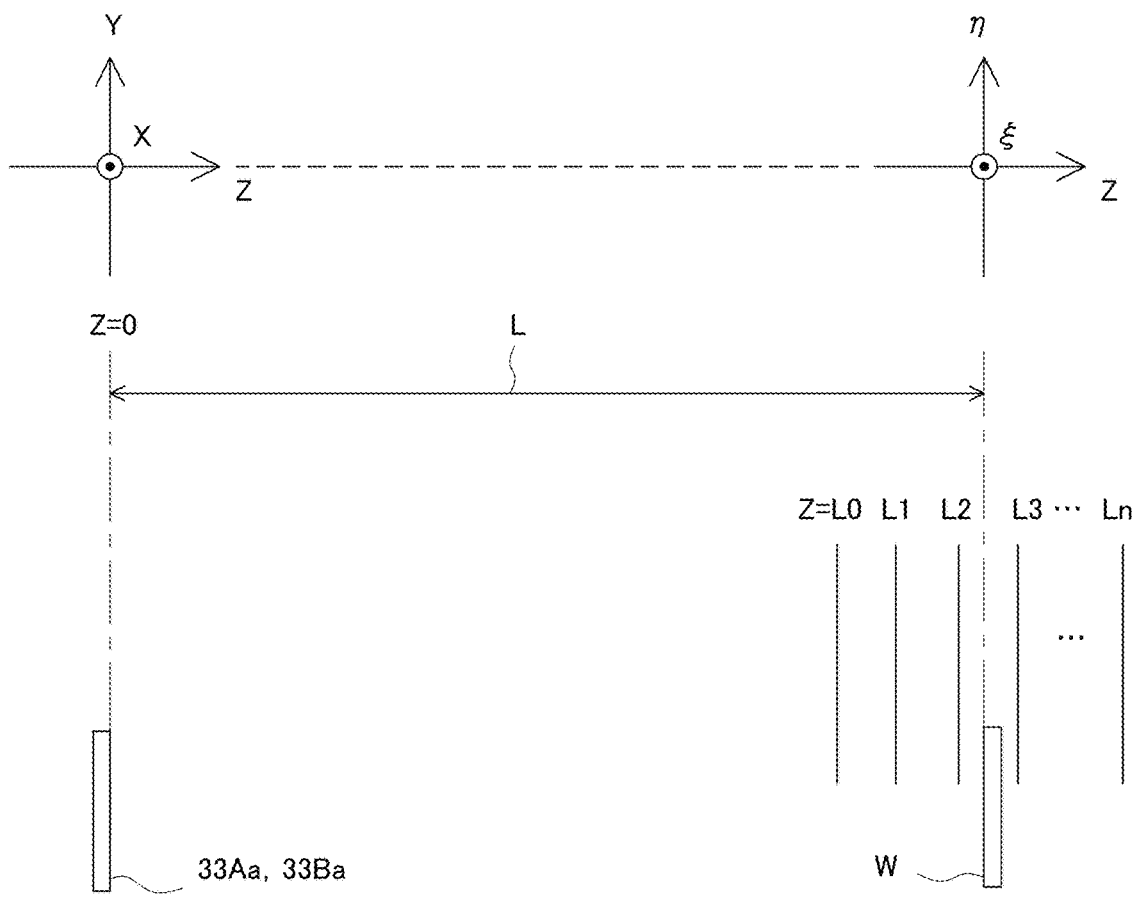
FIG. 6 is a diagram illustrating a positional relationship between a work and an imaging element and the like according to one or more embodiments.

According to one or more embodiments, as shown in FIG. 6 and FIG. 7, complex amplitude data EoL0(ξ,η), EoL1(ξ,η), . . . , EoLn(ξ,η) at respective positions away from the imaging element 33Aa-surface or the imaging element 33Ba-surface by a distance L=L0, L1, L2, . . . , Ln in the z position search area V on the work W are obtained, based on the complex amplitude data Eo(x,y) on the imaging element 33Aa-surface or on the imaging element 33Ba-surface obtained at step S2 described above.

At subsequent step S4, the control device 5 executes a process of obtaining intensity (luminance) images at a plurality of positions in the z direction in the z position search area V on the work W. The image acquisition unit is configured by the function of executing the processing of step S4 according to one or more embodiments.

More specifically, intensity images are obtained respectively from the complex amplitude data EoL0(ξ,η), EoL1(ξ,η), . . . , EoLn(ξ,η) obtained at step S3 described above. When complex amplitude data in the ξ-η plane is expressed as Eo(ξ,η), an intensity image I(ξ,η) in the ξ-η plane may be obtained according to a relational expression of [Math. 7] given below:

$$I(\xi,\eta)=|E_0(\xi,\eta)|^2$$ [Math. 7]

At subsequent step S5, the control device 5 executes a process of determining the position of the work W in the z direction. The position determining unit is configured by the function of executing the processing of step S5 according to one or more embodiments.

More specifically, the position of the z position search area V in the z direction is determined, based on the plurality of intensity images in the z position search area V obtained at step S4 described above. The following describes a method of determining the position of the z position search area V, based on the contrast of the intensity images.

For example, as shown in FIG. 7, a z direction predetermined range Q where the work W is likely to be located is divided by intervals of a measurement range for height measurement, and positions (z=L0, L1, . . . , Ln) away from the imaging element 33Aa-surface or the imaging element 33Ba-surface by a distance L=L0, L1, . . . , Ln in the z direction are set. In the intensity image of the z position search area V at each of the positions in the z direction (z=L0, L1, . . . , Ln), a contrast of luminance between the "z position search area V" and the "remaining area" is calculated. A portion (z=Lm) where an intensity image of the highest contrast is obtained among the intensity images is then extracted. Height information of the z position search area V is obtained by three-dimensional measurement based on complex amplitude data EoLm(ξ,η) at this position (z=Lm). An absolute position of the z position search area V in the z direction is then obtained, based on the "position information of the intensity image (z=Lm)"+"height information of the z position search area V".

The method of determining the position of the z position search area V is not limited to the method based on the contrast of the intensity image described above, but another method may be employed. For example, a method based on the luminance of the intensity image may be employed.

This latter method takes advantage of the characteristic that the luminance image provides the highest luminance in a surface where an object is actually located. More specifically, an average luminance of the z position search area V is calculated with regard to the intensity images of the z position search area V at the respective positions in the z direction (z=L0, L1, . . . , Ln). A position (z=Lm) where an intensity image of the highest average luminance is obtained among the intensity images is then extracted. As in the above case, height information of the z position search area V is obtained by three-dimensional measurement based on the complex amplitude data EoLm(ξ,η) at this position (z=Lm). The absolute position of the z position search area V in the z direction is then obtained, based on the "position information of the intensity image (z=Lm)"+"height information of the z position search area V".

At subsequent step S6, the control device 5 obtains complex amplitude data of the entire measurement area at the position in the z direction of the work W (z position search area V) determined at step S5. The second data obtaining unit is configured by the function of executing the processing of step S6 according to one or more embodiments.

At subsequent step S7, the control device 5 performs three-dimensional measurement. The measurement execution unit is configured by the function of executing the processing of step S7 according to one or more embodiments.

More specifically, the phase φ(ξ,η) of the measurement light and the amplitude A(ξ,η) of the measurement light are calculated according to a relational expression of [Math. 8] given below from the complex amplitude data Eo(ξ,η) of the entire measurement area obtained at step S6 given above.

$$E_0(\xi,\eta)=A(\xi,\eta)e^{i\phi(\xi,\eta)}$$ [Math. 8]

The phase φ(ξ,η) of the measurement light is calculated from a relational expression of [Math. 9] given below:

$$\phi(\xi, \eta) = \arctan \frac{\mathrm{Im}[E_0(\xi, \eta)]}{\mathrm{Re}[E_0(\xi, \eta)]} \qquad [\text{Math. 9}]$$

The amplitude $A(\xi,\eta)$ of the measurement light is calculated from a relational expression of [Math. 10] given below:

$$A(\xi,\eta) = \sqrt{(\mathrm{Re}[E_0(\xi,\eta)])^2 + (\mathrm{Im}[E_0(\xi,\eta)])^2} \qquad [\text{Math. 10}]$$

The control device 5 subsequently executes a phase-height conversion process to calculate height information $z(\xi,\eta)$ that three-dimensionally indicates a convex-concave shape on the surface of the work W.

The height information $z(\xi,\eta)$ is calculated by a relational expression of [Math. 11] given below.

$$Z(\xi, \eta) = \frac{1}{2}\phi(\xi, \eta)\frac{\lambda}{2\pi} \qquad [\text{Math. 11}]$$

Measurement using two different lights having different wavelengths (wavelengths $\lambda_1$ and $\lambda_2$) is equivalent to measurement using a light of a combined wavelength $\lambda_0$, and the measurement range is expanded to $\lambda_0/2$. The combined wavelength $\lambda_0$ is expressed by Equation (M1) given below:

$$\lambda_0 = (\lambda_1 \times \lambda_2)/(\lambda_2 - \lambda_1) \qquad (\text{M1})$$

where $\lambda_2 > \lambda_1$.

For example, when $\lambda_1 = 1500$ nm and $\lambda_2 = 1503$ nm, $\lambda_0 = 751.500$ μm according to Equation (M1) given above, and the measurement range is $\lambda_0/2 = 375.750$ μm.

More specifically, according to one or more embodiments, a phase $\phi_1(\xi,\eta)$ of the measurement light with regard to the first light at coordinates $(\xi,\eta)$ on the surface of the work W is calculated first (as shown by [Math. 9] given above), based on luminance values $I_1(x,y)$, $I_2(x,y)$, $I_3(x,y)$ and $I_4(x,y)$ of the four different interference fringe images with regard to the first light having the wavelength $\lambda_1$ (as shown by [Math. 1] given above).

In measurement with regard to the first light, height information $z(\xi,\eta)$ at the coordinates $(\xi,\eta)$ is expressed by Equation (M2) given below:

$$z(\xi, \eta) = d_1(\xi, \eta)/2 \qquad (\text{M2})$$
$$= [\lambda_1 \times \phi_1(\xi, \eta)/4\pi] + [m_1(\xi, \eta) \times \lambda_1/2]$$

where $d_1(\xi,\eta)$ denotes an optical path difference between the measurement light and the reference light with regard to the first light, and $m_1(\xi,\eta)$ denotes a fringe order with regard to the first light.

The phase $\phi_1(\xi,\eta)$ is accordingly expressed by Equation (M2') given below:

$$\phi_1(\xi,\eta) = (4\pi/\lambda_1) \times z(\xi,\eta) - 2\pi m_1(\xi,\eta) \qquad (\text{M2}')$$

Similarly, a phase $\phi_2(\xi,\eta)$ of the measurement light with regard to the second light at the coordinates $(\xi,\eta)$ on the surface of the work W is calculated (as shown by [Math. 9] given above), based on luminance values $I_1(x,y)$, $I_2(x,y)$, $I_3(x,y)$ and $I_4(x,y)$ of the four interference fringe images with regard to the second light having the wavelength $\lambda_2$ (as shown by [Math. 1] given above).

In measurement with regard to the second light, height information $z(\xi,\eta)$ at the coordinates $(\xi,\eta)$ is expressed by Equation (M3) given below:

$$z(\xi, \eta) = d_2(\xi, \eta)/2 \qquad (\text{M3})$$
$$= [\lambda_2 \times \phi_2(\xi, \eta)/4\pi] + [m_2(\xi, \eta) \times \lambda_2/2]$$

where $d_2(\xi,\eta)$ denotes an optical path difference between the measurement light and the reference light with regard to the second light, and $m_2(\xi,\eta)$ denotes a fringe order with regard to the second light.

The phase $\phi_2(\xi,\eta)$ is accordingly expressed by Equation (M3') given below:

$$\phi_2(\xi,\eta) = (4\pi/\lambda_2) \times z(\xi,\eta) - 2\pi m_2(\xi,\eta) \qquad (\text{M3}')$$

The fringe order $m_1(\xi,\eta)$ with regard to the first light having the wavelength $\lambda_1$ and the fringe order $m_2(\xi,\eta)$ with regard to the second light having the wavelength $\lambda_2$ are determined, based on an optical path difference $\Delta d$ and a wavelength difference $\Delta\lambda$ of the two different lights (having the wavelengths $\lambda_1$ and $\lambda_2$). The optical path difference $\Delta d$ and the wavelength difference $\Delta\lambda$ are respectively expressed by Equations (M4) and (M5) given below:

$$\Delta d = (\lambda_1 \times \phi_1 - \lambda_2 \times \phi_2)/2\pi \qquad (\text{M4})$$

$$\Delta\lambda = \lambda_2 - \lambda_1 \qquad (\text{M5})$$

where $\lambda_2 > \lambda_1$.

In the measurement range of the combined wavelength $\lambda_0$ of the two wavelengths, the relationship between the fringe orders $m_1$ and $m_2$ is classified into the following three cases. Different computation expressions are employed to determine the fringe orders $m_1(\xi,\eta)$ and $m_2(\xi,\eta)$ in the respective cases. The following describes a technique of determining, for example, the fringe order $m_1(\xi,\eta)$. A similar technique may be employed to determine the fringe order $m_2(\xi,\eta)$.

For example, in the case of "$-\pi < \phi_1 - \phi_2 < -\pi$", "$m_1 - m_2 = -1$". In this case, $m_1$ is expressed by Equation (M6) given below:

$$m_1 = (\Delta d/\Delta\lambda) - (\lambda_2/\Delta\lambda) \qquad (\text{M6})$$
$$= (\lambda_1 \times \phi_1 - \lambda_2 \times \phi_2)/2\pi(\lambda_2 - \lambda_1) - \lambda_2/(\lambda_2 - \lambda_1)$$

In the case of "$-\pi < \phi_1 - \phi_2 < \pi$", "$m_1 - m_2 = 0$". In this case, $m_1$ is expressed by Equation (M7) given below:

$$m_1 = \Delta d/\Delta\lambda \qquad (\text{M7})$$
$$= (\lambda_1 \times \phi_1 - \lambda_2 \times \phi_2)/2\pi(\lambda_2 - \lambda_1)$$

In the case of "$\phi_1 - \phi_2 > \pi$", "$m_1 - m_2 = +1$". In this case, $m_1$ is expressed by Equation (M8) given below:

$$m_1 = (\Delta d/\Delta\lambda) + (\lambda_2/\Delta\lambda) \qquad (\text{M8})$$
$$= (\lambda_1 \times \phi_1 - \lambda_2 \times \phi_2)/2\pi(\lambda_2 - \lambda_1) + \lambda_2/(\lambda_2 - \lambda_1)$$

The height information $z(\xi,\eta)$ is calculated according to Equation (M2) or (M3) given above, based on the fringe order $m_1(\xi,\eta)$ or $m_2(\xi,\eta)$ thus obtained.

Figure 9:
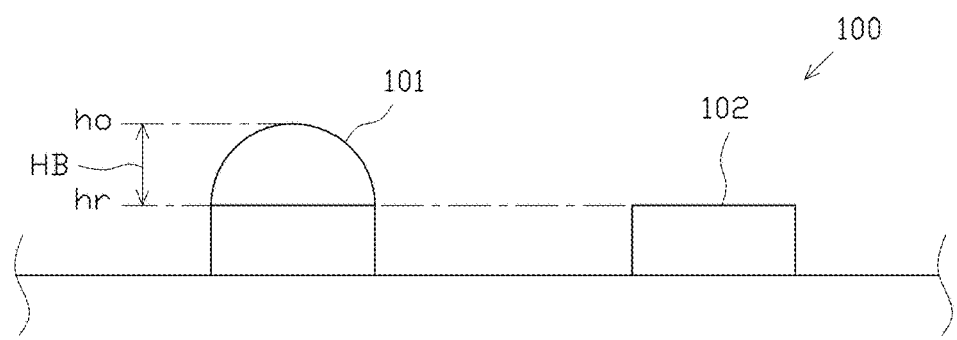
FIG. 9 is a diagram illustrating three-dimensional measurement of a bump according to one or more embodiments.

For example, when the work W is a wafer substrate 100 (as shown in FIG. 8 and FIG. 9) and a bump 101 is a measurement object, a height HB of the bump 101 relative to a patterned part 102 that is a measurement reference surface is determined by subtracting an absolute height hr of the patterned part 102 in the periphery of the bump 101 from an absolute height ho of the bump 101 [HB=ho−hr]. The absolute height hr of the patterned part 102 may be, for example, an absolute height at any one point on the patterned part 102 or an average value of absolute heights in a predetermined range on the patterned part 102. The "absolute height ho of the bump 101" and the "absolute height hr of the patterned part 102" may also be determined as the height information $z(\xi,\eta)$.

The measurement result (height information) of the work W thus determined is stored into the calculation result storage device 55 of the control device 5.

As described above in detail, the configuration of one or more embodiments first obtains complex amplitude data at a plurality of positions in the optical axis direction not with regard to the entire measurement area of the work W but with regard to only the z position search area V set in advance as part in the measurement area, and searches for and determines the focused optimum position of the work W (z position search area V), based on the obtained complex amplitude data. The configuration of one or more embodiments subsequently obtains complex amplitude data with regard to the entire measurement area of the work W at the determined position and performs measurement of the measurement area.

This configuration reduces the processing load for obtaining data required for measurement of the measurement area and shortens the time period required for such processing. As a result, this improves the measurement accuracy and improves the measurement efficiency.

Furthermore, the configuration of one or more embodiments specifies the position in the z direction of the work W (z position search area V), obtains the complex amplitude data of the entire measurement area at the position and performs the measurement. This configuration can obtain the optimum data of the higher accuracy focused on the work W (z position search area V), compared with a configuration that simply extracts optimum data among a plurality of different complex amplitude data obtained at predetermined intervals (measurement ranges). As a result, this configuration further improves the measurement accuracy.

The configuration of one or more embodiments causes the first light having the wavelength $\lambda_1$ to enter the first surface 20a of the polarizing beam splitter 20 and causes the second light having the wavelength $\lambda_2$ to enter the second surface 20b of the polarizing beam splitter 20. This configuration causes the reference light and the measurement light with regard to the first light and the reference light and the measurement light with regard to the second light to be respectively split into different polarized light components (P-polarized light or S-polarized light). The first light and the second light entering the polarizing beam splitter 20 accordingly do not interfere with each other but are separately emitted from the polarizing beam splitter 20. There is accordingly no need to divide the light emitted from the polarizing beam splitter 20 into the first light and the second light by a predetermined separation unit.

As a result, this configuration enables two different lights having wavelengths close to each other to be used as the first light and the second light and further expands the measurement range in three-dimensional measurement. Additionally, this configuration enables imaging of the output light with regard to the first light and imaging of the output light with regard to the second light to be executed simultaneously. This shortens the total imaging time and improves the measurement efficiency.

The present invention is not limited to the description of the above embodiments but may also be implemented, for example, by configurations described below. The present invention may further be implemented by other applications and other modifications that are not specifically described below.

(a) The work W as the measurement object is not limited to the wafer substrate 100 illustrated in the above embodiments. For example, a printed circuit board with solder paste printed thereon may be the work W (measurement object).

A bump inspection device or a solder printing inspection device equipped with an inspection unit configured to inspect the good/poor quality of bump or solder paste as the measurement object according to previously set good/poor quality determination criteria may be provided with the measurement device 1.

(b) The above embodiments do not specifically describe the predetermined measurement area of the work W. The entire area of the work W may be set as the measurement area or part of the work W may be set as the measurement area according to the size of the work W.

For example, the placement structure 24 which the work W is placed on may be configured to be movable. The surface of the work W may be divided into a plurality of measurement areas, and shape measurement of the entire work W may be implemented by performing shape measurement multiple times for the respective measurement areas with successively changing the measurement area.

(c) The configuration of the interference optical system (predetermined optical system) is not limited to that of the above embodiments. For example, the above embodiments employ the optical configuration of a Michelson interferometer as the interference optical system. This is, however, not essential, but any other optical configuration, for example, an optical configuration of a Mach-Zehnder interferometer or an optical configuration of a Fizeau interferometer, may be employed to divide incident light into reference light and measurement light and perform measurement of the work W.

(d) The above embodiments use two different types of lights having different wavelengths to perform measurement of the work W. This is, however, not essential, but only one type of light may be used to perform measurement of the work W.

The configuration of using two different types of lights having different wavelengths is not limited to the configuration of the above embodiments. Like a conventional measurement device, a modification may be configured to cause combined light of first wavelength light and second wavelength light to enter an interference optical system, to cause interfering light emitted from the interference optical system to be subjected to wavelength separation by a predetermined optical separating unit (for example, a dichroic mirror), so as to obtain interfering light with regard to the first wavelength light and interfering light with regard to the second wavelength light, and to perform measurement of the work W, based on interference fringe images obtained by individually taking images of the interfering lights with regard to the respective wavelength lights.

Another modification may be configured to perform measurement of the work W by using three or more different types of lights having different wavelengths by combining a configuration of causing an overlapped state of two different types of lights that are emitted from two light sources and that have different wavelengths to enter an interference optical system, causing light emitted from the interference optical system to be subjected to wavelength separation by an optical separating unit, and individually taking images of interfering lights with regard to the respective wavelength lights, with the configuration of one or more embodiments.

(e) The configurations of the projection optical systems 2A and 2B are not limited to those of the embodiments described above. For example, the above embodiments are configured to radiate the light having the wavelength $\lambda_1$ of 1500 nm from the first projection optical system 2A and to radiate the light having the wavelength $\lambda_2$ of 1503 nm from the second projection optical system 2B. The wavelengths of the respective lights are, however, not limited to those of the above embodiments. The wavelength difference between two lights is made smaller in order to expand the measurement range.

(f) The above embodiments are configured to obtain four different interference fringe images having phases that differ from each other by 90 degrees each, with regard to the first light and the second light. The number of times of phase shift and the amount of phase shift are, however, not limited to those of the above embodiments. For example, a modification may be configured to obtain three different interference fringe images having phases that differ from each other by 120 degrees (or 90 degrees) and perform measurement of the work W.

(g) The above embodiments employ the polarizers 32A and 32B configured to change the transmission axis direction, as the phase shift unit. The configuration of the phase shift unit is, however, not limited to the above embodiments.

For example, a modification employed may be configured to physically change the optical path length by moving the reference surface 23 along the optical axis by means of a piezoelectric element or the like.

In this modified configuration and the configuration of the above embodiments, a certain time period is required to obtain all interference fringe images required for measurement. This increases the measurement time and is likely to decrease the measurement accuracy, due to the potential influence of fluctuation of the air, vibration and the like.

For example, according to one modified configuration, the first imaging system 4A may be provided with a spectroscopic unit (for example, prism) configured to divide combined light (reference light component and measurement light component) with regard to the first light transmitted through the quarter wave plate 31A into four lights, and may also be provided with a filter unit configured to produce different phase differences to the four lights emitted from the spectroscopic unit, in place of the first polarizer 32A, as the phase shift unit. Images of the four lights transmitted through the filter unit may be taken simultaneously by the first camera 33A (or by a plurality of cameras). The second imaging system 4B may have a similar modified configuration.

This modified configuration enables all interference fringe images required for measurement to be obtained simultaneously. More specifically a total of eight different interference fringe images with regard to two different types of lights may be obtained simultaneously. As a result, this significantly shortens the total imaging time to remarkably improve the measurement efficiency, while improving the measurement accuracy.

(h) The above embodiments are configured to obtain the complex amplitude data and the like at the intervals of the measurement range for height measurement in the process of determining the position of the work W (z position search area V) in the z direction. This is, however, not essential, but a modification may be configured to obtain the complex amplitude data and the like at intervals of, for example, a focusing range.

(i) The above embodiments are configured to perform three-dimensional measurement at step S7, based on the complex amplitude data of the entire measurement area obtained at step S6. In place of this configuration or in addition to this configuration, there may be a modified configuration of obtaining intensity images of the entire measurement area and perform two-dimensional measurement, based on the complex amplitude data of the entire measurement area obtained at step S6.

Figure 10:
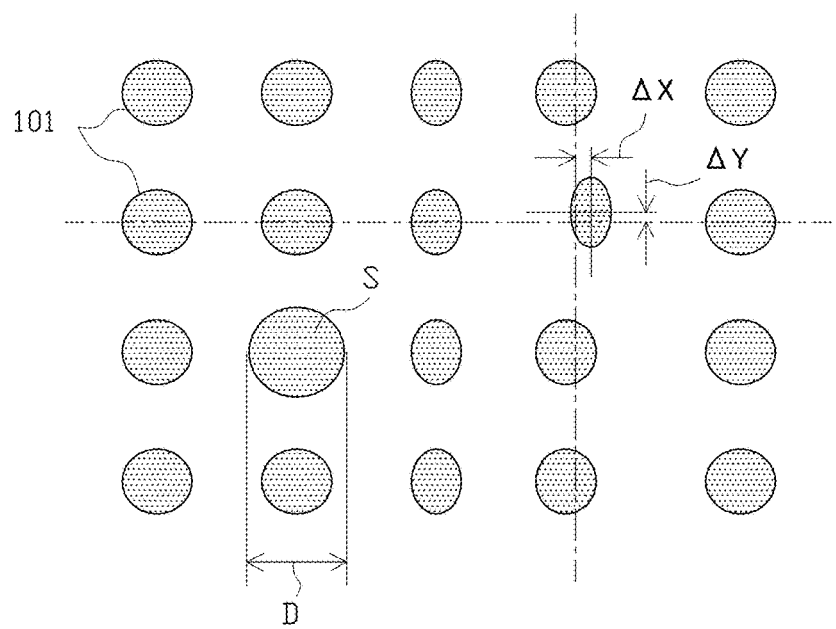
FIG. 10 is a diagram illustrating three-dimensional measurement of bumps according to one or more embodiments.

In the case of performing only two-dimensional measurement at step S7, two-dimensional inspection may be performed by comparing, for example, positional misalignments $\Delta x$ and $\Delta y$, an outer diameter D and an area S of a bump 101 (as shown in FIG. 10) as the measurement object with reference values set in advance and determining the good/poor quality of the bump 101, based on determination of whether the results of the comparison are within allowable range.

In the case of performing both two-dimensional measurement and three-dimensional measurement, comprehensive measurement by combination of multiple different types of measurements may be performed by specifying a position where the bump 101 as the measurement object is located, based on the result of two-dimensional measurement (two-dimensional inspection) or by mapping intensity images to three-dimensional data obtained by three-dimensional measurement.

(j) The above embodiments use the cameras equipped with lenses. The lens is, however, not essential. A focused image may be obtained by calculation even when cameras without lenses are used in one or more embodiments.

(k) The above embodiments are configured to specify the position in the z direction of the work W (z position search area V), obtain the complex amplitude data of the entire measurement area at the specified position and perform measurement. The position in the z direction where the complex amplitude data of the entire measurement area is obtained is, however, not limited to the above embodiments. For example, a modified configuration may obtain complex amplitude data of the entire measurement area at a position (z=Lm) where a most focused intensity image is obtained and perform measurement.

(l) In the wafer substrate 100 illustrated in the above embodiments, the patterned part 102 as the reference surface of height measurement of the bump 101 is set as the z position search area V. The z position search area V may not be necessarily a portion serving as a reference surface but may be another portion.

(m) Although not being specifically described in the above embodiments, the z position search area V may be set at a plurality of different positions. Setting the plurality of z position search areas V enables the optimum position where the complex amplitude data of the entire measurement area are to be obtained, to be found more readily.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims

REFERENCE SIGNS LIST

1 . . . measurement device, 2A . . . first projection optical system, 2B . . . second projection optical system, 3 ... interference optical system, 4A ... first imaging system, 4B ... second imaging system, 5 ... control device, 11A ... first light emitter, 11B ... second light emitter, 12A ... first light isolator, 12B ... second light isolator, 13A ... first non-polarizing beam splitter, 13B ... second non-polarizing beam splitter, 20 ... polarizing beam splitter, 20a ... first surface, 20c ... third surface, 20b ... second surface, 20d ... fourth surface, 21, 22 ... quarter wave plates, 23 ... reference surface, 24 ... placement structure, 31A ... quarter wave plate, 31B ... quarter wave plate, 32A ... first polarizer, 32B ... second polarizer, 33A ... first camera, 33B ... second camera, 33Aa, 33Ba ... imaging elements, 100 ... wafer substrate, 101 ... bump, 102 ... patterned part, V ... z position search area, W ... work

The invention claimed is:

1. A measurement device comprising:
an optical system that:
splits incident light into two lights,
emits one of the two lights as measurement light to a measurement object and the other as reference light to a reference surface, and
recombines the two lights and emits combined light as output light;
a light emitter that emits predetermined light entering the optical system;
an imaging system that takes an image of the output light emitted from the optical system; and
a processor that executes measurement with regard to a predetermined measurement area of the measurement object, based on an interference fringe image taken by the imaging system, wherein
the processor:
obtains a plurality of complex amplitude data at a predetermined position in an optical axis direction at predetermined intervals in at least a predetermined range in the optical axis direction, with regard to a specific area set in advance in the measurement area, based on the interference fringe image taken by the imaging system;
obtains a plurality of intensity images at the predetermined intervals with regard to the specific area, from the plurality of complex amplitude data at the predetermined intervals with regard to the specific area;
determines the predetermined position in the optical axis direction based on the plurality of obtained intensity images;
obtains complex amplitude data at the determined position with regard to the entire measurement area; and
executes measurement with regard to the measurement area based on the obtained complex amplitude data.

2. The measurement device according to claim 1, wherein the processor determines a position of the specific area in the optical axis direction based on the plurality of obtained intensity images.

3. The measurement device according to claim 2, wherein the specific area is a basis for measurement in the optical axis direction with regard to the measurement area.

4. The measurement device according to claim 1, wherein a plurality of specific areas is set at a plurality of positions.

5. The measurement device according to claim 2, wherein a plurality of specific areas is set at a plurality of positions.

6. The measurement device according to claim 3, wherein a plurality of specific areas is set at a plurality of positions.

7. The measurement device according to claim 1, further comprising:
a polarizer that produces a relative phase difference between the reference light and the measurement light, wherein
the processor executes measurement with regard to the predetermined measurement area of the measurement object, based on a plurality of interference fringe images obtained by the imaging system that takes images of the output light having a phase shifted by a plurality of times by the polarizer.

8. The measurement device according to claim 2, further comprising:
a polarizer that produces a relative phase difference between the reference light and the measurement light, wherein
the processor executes measurement with regard to the predetermined measurement area of the measurement object, based on a plurality of interference fringe images obtained by the imaging system that takes images of the output light having a phase shifted by a plurality of times by the polarizer.

9. The measurement device according to claim 3, further comprising:
a polarizer that produces a relative phase difference between the reference light and the measurement light, wherein
the processor executes measurement with regard to the predetermined measurement area of the measurement object, based on a plurality of interference fringe images obtained by the imaging system that takes images of the output light having a phase shifted by a plurality of times by the polarizer.

10. The measurement device according to claim 1, wherein the light emitter comprises:
a first light emitter that emits first light including polarized light of a first wavelength and entering the optical system; and
a second light emitter that emits second light including polarized light of a second wavelength and entering the optical system, and
the imaging system comprises:
a first imaging system that takes the image of output light emitted from the optical system when the first light enters the optical system; and
a second imaging system that takes the image of output light emitted from the optical system when the second light enters the optical system.

11. The measurement device according to claim 2, wherein the light emitter comprises:
a first light emitter that emits first light including polarized light of a first wavelength and entering the optical system; and
a second light emitter that emits second light including polarized light of a second wavelength and entering the optical system, and
the imaging system comprises:
a first imaging system that takes the image of output light emitted from the optical system when the first light enters the optical system; and
a second imaging system that takes the image of output light emitted from the optical system when the second light enters the optical system.

12. The measurement device according to claim 3,
wherein the light emitter comprises:
- a first light emitter that emits first light including polarized light of a first wavelength and entering the optical system; and
- a second light emitter that emits second light including polarized light of a second wavelength and entering the optical system, and the imaging system comprises:
- a first imaging system that takes the image of output light emitted from the optical system when the first light enters the optical system; and
- a second imaging system that takes the image of output light emitted from the optical system when the second light enters the optical system.

13. The measurement device according to claim 1,
wherein the measurement object is a wafer substrate on which a bump is formed.

14. The measurement device according to claim 2,
wherein the measurement object is a wafer substrate on which a bump is formed.

15. The measurement device according to claim 3,
wherein the measurement object is a wafer substrate with on which a bump is formed.

* * * * *